United States Patent [19]

Loudon

[11] Patent Number: 4,834,656
[45] Date of Patent: May 30, 1989

[54] ADJUSTABLE COMPOSITE DENTAL CROWN AND ASSOCIATED PROCEDURE

[76] Inventor: Merle E. Loudon, 514 15th NE., East Wenatchee, Wash. 98801

[21] Appl. No.: 66,502

[22] Filed: Jun. 26, 1987

[51] Int. Cl.[4] .............................................. A61C 5/00
[52] U.S. Cl. .................................. 433/215; 433/218; 433/223
[58] Field of Search ..................... 433/218, 219, 222.1, 433/223, 215, 6

[56] References Cited

U.S. PATENT DOCUMENTS

| | | | |
|---|---|---|---|
| 504,126 | 8/1893 | Durr | 433/219 |
| 2,154,499 | 4/1939 | Eisenstein | 433/219 |
| 2,194,790 | 3/1940 | Gluck | 433/223 |
| 2,770,040 | 11/1956 | Moyer | 433/218 |
| 4,211,008 | 7/1980 | Lerman | 433/6 |
| 4,710,127 | 12/1987 | Bellavia et al. | 433/218 |

FOREIGN PATENT DOCUMENTS 1147583  6/1983  Canada .................................. 433/6

Primary Examiner—John J. Wilson
Attorney, Agent, or Firm—Fleit, Jacobson, Cohn & Price

[57] ABSTRACT

Dental crowns with cap portions of adjustable height are applied to selected natural teeth of a dental patient to prevent bite closing occlusion until the other unaltered teeth have erupted to reestablish bite with respect to a new desired occlusal scheme to thereby correctively change mandibular/condyle position.

11 Claims, 1 Drawing Sheet

ADJUSTABLE COMPOSITE DENTAL CROWN AND ASSOCIATED PROCEDURE

BACKGROUND OF THE INVENTION

This invention relates to a dental procedure for correcting malocclusions involving the use of adjustable dental crowns.

Malocclusion development is often detected in children by observation of deep overbite and bear on primary maxillary cuspids and premolars. Subsequent observations of lateral tongue splinting and lack of proper growth indicate further developing malocclusion characterized as a loss of vertical dimension. Such vertical loss if not corrected early may result in several problems during later life including improper muscle development, myofascial pain and tempero mandibular joint symptoms. The latter symptoms may result from short crown length of the permanent lower bicuspids and first molars, allowing the second molars to erupt higher than the first molars.

It is therefore an object of the present invention to provide a method of correcting early loss of vertical dimension because of malocclusion which leads to the dental problems aforementioned.

A further object in accordance with the preceding object is to provide readily available and inexpensive means for effective correction of the vertical loss type of malocclusion aforementioned.

SUMMARY OF THE INVENTION

A basic concept associated with the malocclusion correcting method or procedure of the present invention, is the use of readily available dental crown technology for effecting changes in mandibular/condyle position within the oral cavity of a dental patient. The manufacture and application of dental crowns to prepared or altered natural teeth is, of course, well known as disclosed by way of example in U.S. Pat. Nos. 504,126, 2,154,499 and 4,504,230 to Durr, Eisenstein and Patch, respectively. However, none of such prior art disclosures suggest excess vertical crown buildup and adjustments for malocclusion correcting purposes. On the contrary, crown adjustment after fitting onto a natural tooth is suggested in the Patch patent for the express purpose of achieving a previously established centric bite or occlusal position. In contrast thereto, application of the crowns in accordance with the present invention is designed to change the previously established position of the mandible and condyles under an existing undesirable occlusal scheme.

In accordance with one embodiment of the present invention, vertical dimension loss in a young dental patient is determined by forward movement of the mandible to achieve a predetermined amount of overbite, such as one millimeter. Both sides of the bite are then measured to determine the amount of vertical spacing between molars and the build-up required to maintain such open bite condition for a normal muscle balance. Such vertical build-up is achieved by applying dental crowns to the lower first and second molars thereby adding the requisite vertical occlusal height so as to maintain the anterior central overbite condition in accordance with the aforementioned measurements. Such normal and more open bite condition is maintained by the applied dental crowns, or subsequently readjusted by dimensional modification of the crowns. The crowns when applied to the teeth are finished to establish a common occlusal contact plane corresponding to a new desirable occlusal scheme. The anterior central overbite condition aforementioned is maintained until full eruption occurs with respect to the first permanent molars toward such common occlusal contact plane.

BRIEF DESCRIPTION OF DRAWING FIGURES

These together with other objects and advantages which will become subsequently apparent reside in the details of construction and operation as more fully hereinafter described and claimed, reference being had to the accompanying drawings forming a part hereof, wherein like numerals refer to like parts throughout.

DETAILED DESCRIPTION OF PREFERRED EMBODIMENT

Figure 1:
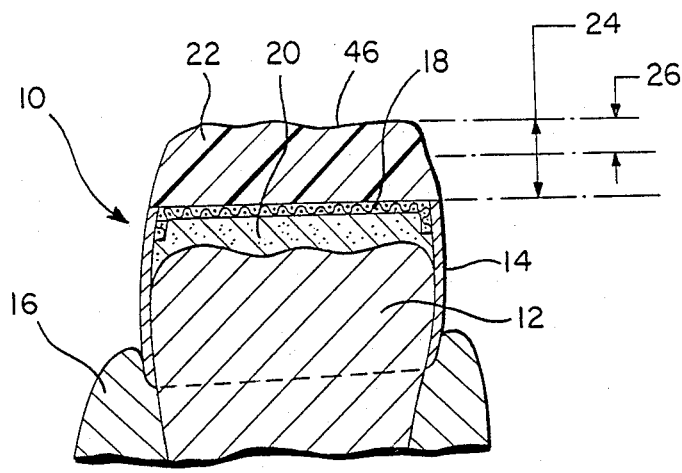
FIG. 1 is a side section view through a dental crown applied to a prepared natural tooth in accordance with the present invention.

Referring now to the drawing in detail, FIG. 1 illustrates a finished crown generally referred to by reference numeral 10, applied to a natural tooth 12 which was previously prepared for crown reception. The crown 10 consists of a metallic sleeve 14, preferably made of stainless steel, crimped into a tight fit about the tooth 12 and extending below the gingival 16. The sleeve 14 has a mesh wire grid 18 welded thereto at its upper end above the prepared tooth. The grid 18 retains a body of composite bonding material 20 through which the sleeve 14 is attached to the tooth 12. The sleeve 14 is bonded to a crown cap or top portion 22 made of a material such as a composite plastic, acrylic or resin. The material of the crown top 22 has an adjustable capability in that additional material may be added thereto or removed therefrom for height readjustment purposes.

Different size crowns 10 may be prefabricated to provide a set of sizes from which selections are made to most closely fit a crown onto a prepared natural teeth. The crown top portion 22 will have a thickness dimension 24 of four to five millimeters to exceed by some amount 26 the already established occlusal plane or bite of a person. Thus, the crowns when applied to selected teeth will hold the jaws somewhat open or spaced from the closed position previously established by occlusion of the natural teeth.

Figure 2:
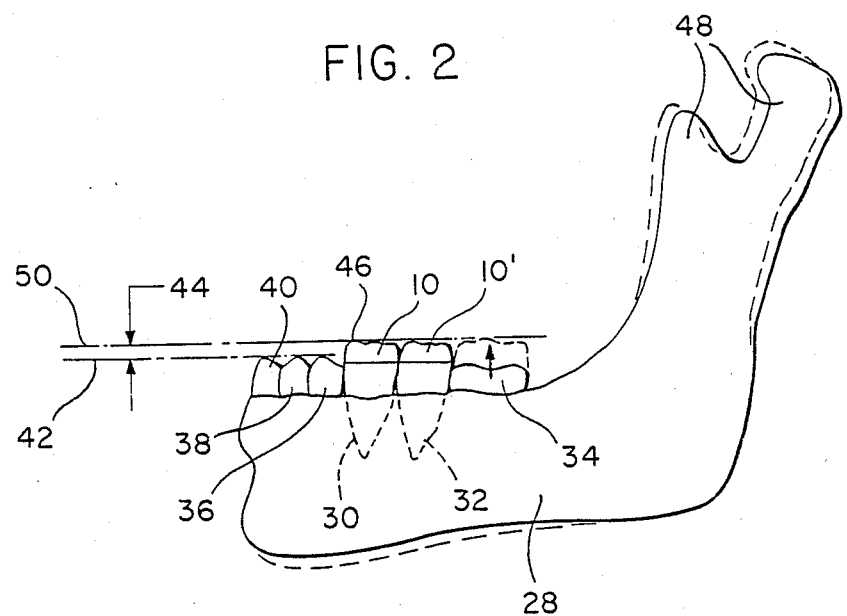
FIG. 2 is a side elevation view of a mandible with permanent natural teeth carried thereon, having dental crowns applied to the first and second primary molars in accordance with the malocclusion correcting method of the present invention.

By way of example, FIG. 2 illustrates a typical lower jaw or mandible 28 in side elevation carrying natural permanent teeth including the first and second primary molars 30 and 32, first permanent molars 34, cuspid 36, lateral incisor 38 and the anterior incisor 40. The first and second primary molars 30 and 32 have crowns 10 and 10' applied thereto in accordance with the present invention as described in detail with respect to FIG. 1. Accordingly, the crowns 10 and 10' will prevent closing of the mandible to a previously established occlusion plane 42 by a vertical distance 44 determined by the top surfaces 46 of the crowns 10 and 10'.

In the previously established occlusal condition within the oral cavity of a person, the mandible 28 as shown by solid line in FIG. 2 together with its condyles 48 will have a predetermined mandibular/condyle position or orientation. With the crowns 10 and 10' applied to prevent full closing of the jaws to the previous mandibular/condyle position, the first permanent molars 34 will erupt until a plane of occlusion 50 is established in common with the crown surfaces 46.

Adjacent crowns 10 and 10' are finished by use of burrs, disks and rubber points or wheels for equal occlusal contact at their surfaces 46 to establish one millimeter of anterior central overbite, in accordance with one embodiment of the invention. When full eruption of the molars 34 occurs, the mandibular/condyle position will have correspondingly changed as shown by dotted line in FIG. 2. Thus, by proper dimensional selection of crown heights and possible readjustment of the crown heights by the addition or removal of material from the top portion 22, a desired corrective change in mandibular/condyle position may be achieved.

Although FIG. 2 shows crowns applied to the lower first and second primary molars 30 and 32, it should be appreciated that such crowns may be applied to other permanent natural teeth for eruption of natural teeth other than the first permanent molars 34, in order to achieve corrective change in mandibular/condyle position in accordance with the procedure of the present invention.

It will also be apparent from the foregoing description that the dental crowns 10 and 10' applied to the lower first and second primary molars, by way of example in accordance with the present invention, will hold the mandible 28 more open than conventional crowns because of the extra thickness of the crown tops 22. Such crown tops are dimensioned by preselection and/or readjustment to establish a precise open bite distance as determined by the dentist. The vertical dimension of the crown tops thus regulate the relationship of the mandible/condyles 48 to their cranial fossa and the extent of eruption of certain of the teeth such as the first permanent molars 34.

Some of the benefits achieved by the procedure of the present invention include reduction of large overbite, increased vertical eruption of certain teeth, corrective change in tongue position, more normal placement of the mandibular condyles in the fossa, proper placement of the tempero mandibular disk, more normal muscle balance and less orthodontic vertical correction at a later date.

The foregoing is considered as illustrative only of the principles of the invention. Further since numerous modifications and changes will readily occur to those skilled in the art, it is not desired to limit the invention to the exact construction and procedures shown and described, and, accordingly, all suitable modifications and equivalents may be resorted to, falling within the scope of the invention.

What is claimed is:

1. A method of correctively changing the mandibular/condyle position within the oral cavity of a dental patient having natural teeth with respect to which occlusion is established under an undesirable occlusal scheme, said method utilizing at least one dental crown and including the steps of: altering one of the natural teeth for reception of said dental crown; applying said dental crown to the altered one of the natural teeth; dimensionally adjusting the applied crown to establish an open bite condition with respect to a new desired occlusal scheme; and maintaining said open bite condition of the dimensionally adjusted crown until the unaltered natural teeth have erupted to reestablish occlusion under the new desired occlusal scheme.

2. The method of claim 1 wherein said dental crown is formed by a metallic sleeve applied to the altered one of the natural teeth, a cap made of adjustable surface material and a wire mesh interface between said cap and the sleeve, said step of adjusting the applied crown comprising: changing the amount of the adjustable surface material forming the cap after the dental crown is applied.

3. A method of correctively changing the mandibular/condyle position within the oral cavity of a dental patient having natural teeth with respect to which occlusion is established, said method utilizing at least one dental crown and including the steps of: applying said dental crown to one of the natural teeth; adjusting the applied crown to a vertical dimension corresponding to an open bite condition; maintaining said open bite condition corresponding to the adjusted vertical dimension of the applied crown until other of the natural teeth have erupted to reestablish occlusion; and readjusting the vertical dimension of the applied dental crown for continued eruption of said other of the natural teeth until the reestablished occlusion corresponds to a desired corrected mandibular/condyle position.

4. The method of claim 3 wherein said dental crown is formed by a metallic sleeve, a cap made of adjustable surface material and a wire mesh interface between said cap and the sleeve, said step of readjusting the applied crown comprising: changing the amount of the adjustable surface material forming the cap.

5. The method of claim 1 wherein, said step of applying the dental crown includes: preparation of said one of the teeth; and crimping the sleeve on the prepared one of the teeth.

6. A method of correctively changing the mandibular/condyle position within the oral cavity of a dental patient having natural teeth with respect to which occlusion is established under an undesirable occlusal scheme, said method utilizing dental crowns and including the steps of: selecting the natural teeth to be altered for application of the dental crowns thereto; altering the selected natural teeth dimensionally selecting the applied dental crowns applied to the altered natural teeth to establish an open bite condition; and maintaining the open bite condition by means of the applied crowns until the unaltered natural teeth have erupted to reestablish occlusion under a new desirable occlusal scheme corresponding to corrected mandibular/condyle position.

7. The method of claim 6 wherein said dental crowns have top portions made of adjustable occlusal surface material and including the step of: dimensionally changing the dental crowns by removal of or adding the occlusal surface material to the top portions after the dental crowns are applied to the altered natural teeth.

8. The method of claim 7 wherein the selected ones of the natural teeth are lower first and second molars.

9. The method of claim 8 wherein said steps of selecting the natural teeth to be altered and the applied dental crowns includes the steps of: forwardly displacing the mandible to an anterior central overbite position prior to application of the dental crowns; measuring vertical spacing of the lower first and second molars from occlusal contact in said overbite position to determine vertical occlusal height of the dental crowns.

10. The method of claim 6 wherein the selected ones of the natural teeth are lower first and second primary molars and the other of the natural teeth are lower first permanent molars.

11. The method of claim 10 wherein said steps of selecting the natural teeth to be altered and the applied dental crowns includes the steps: forwardly displacing the mandible to an anterior central overbite position prior to application of the dental crowns; and measuring vertical spacing of the lower first and second molars from occlusal contact in said overbite position to determine vertical occlusal height of the dental crowns.

* * * * *